(12) United States Patent
Chakravortty et al.

(10) Patent No.: US 8,444,999 B2
(45) Date of Patent: May 21, 2013

(54) **MUTATED *SALMONELLA TYPHI* STRAIN AND USE THEREOF IN A VACCINE**

(75) Inventors: Dipshikha Chakravortty, Bangalore (IN); Vidya Devi Negi, Bangalore (IN)

(73) Assignee: Indian Institute of Science, Bangalore (IN)

( * ) Notice: Subject to any disclaimer, the term of this patent is extended or adjusted under 35 U.S.C. 154(b) by 292 days.

(21) Appl. No.: 12/674,568

(22) PCT Filed: Aug. 22, 2008

(86) PCT No.: PCT/IN2008/000524
§ 371 (c)(1),
(2), (4) Date: Feb. 22, 2010

(87) PCT Pub. No.: WO2009/025000
PCT Pub. Date: Feb. 26, 2009

(65) Prior Publication Data
US 2011/0117132 A1    May 19, 2011

(30) Foreign Application Priority Data
Aug. 23, 2007    (IN) ............... 1889/CHE/2007

(51) Int. Cl.
*A06K 39/02*    (2006.01)
*C12N 15/00*    (2006.01)
*C12N 15/74*    (2006.01)
*C12N 1/12*    (2006.01)
*C12N 1/20*    (2006.01)

(52) U.S. Cl.
USPC ............ 424/235.1; 424/234.1; 435/320.1; 435/252.1; 435/252.3; 435/471; 435/477

(58) Field of Classification Search
None
See application file for complete search history.

(56) References Cited

FOREIGN PATENT DOCUMENTS
GB    1291214 A    10/1972
WO    WO 03/031599    4/2003

OTHER PUBLICATIONS

VIVOTIF (Typhoid vaccine live oral Ty21a) product insert, Aug. 2006.*
Miscarriage. http://www.ncbi.nlm.nih.gov/pubmedhealth/PMH0002458/ retrieved Jun. 27, 2012.*
Datsenko, K.A., et al., "One-step Inactivation of Chromosomal Genes in *Escherichia coli* K-12 Using PCR Products," *Proc. of the National Academy of Sciences of the USA*, Jun. 6, 2000, pp. 6640-6645, vol. 97, No. 12.
Eguchi, Y. et al., "A Novel Mechanism for Connecting Bacterial Two-Component Signal-Transduction Systems," *Trends in Biochemical Sciences*, Feb. 2005, pp. 70-72, vol. 30, No. 2.
Ivanoff, B., "Vaccination against Typhoid Fever: Present Status," *Bulletin of the World Health Organization*, 1994, pp. 957-971, vol. 72, No. 6.
Khan, S. et al., "*Salmonella typhi* and *S. typhimurium* Derivatives Harbouring Deletions in Aromatic Biosynthesis and *Salmonella* Pathogenicity Island-2 (SPI-2) Genes as Vaccines and Vectors," *Vaccine*, Jan. 2003, pp. 538-548, vol. 21, Issues 5-6.
Kirkpatrick, B.D. et al., "Evaluation of *Salmonella enterica* Serovar *typhi* (Ty2 aroC-ssaV-) M01ZH09, with a Defined Mutation in the *Salmonella* Pathogenicity Island 2, as a Live, Oral Typhoid Vaccine in Human Volunteers," *Vaccine*, Jan. 2006, pp. 116-123, vol. 24, Issue 2.
Miller, S.I. et al., "The PhoP Virulence Regulon and Live Oral *Salmonella* Vaccines," *Vaccine*, 1993, pp. 122-125 vol. 11, Issue 2.
Nagy, G. et al., "Oral Immunization with an rfaH Mutant Elicits Protection against Salmonellosis in Mice," *Infection and Immunity*, Jul. 2004, pp. 4297-4301, vol. 72, No. 7.
Negi, V.D. et al., "*Salmonella enterica* Serovar *typhimurium* Strain Lacking pmrG-HM-D Provides Excellent Protection against Salmonellosis in Murine Typhoid Model," *Vaccine*, Jul. 20, 2007, pp. 5315-5323, vol. 25, Nr. 29.
PCT International Search Report and Written Opinion, PCT Application No. PCT/IN2008/000524, Dec. 11, 2008, seven pages.
Tacket, C. et al., "Safety of Live Oral *Salmonella typhi* Vaccine Strains with Deletions in htrA and aroC aroD and Immune Response in Humans," *Infection and Immunity*, Feb. 1997, pp. 452-456, vol. 65.
Tang, I.K., et al., "Characterization of a Highly Attenuated *Salmonella enterica* Serovar *typhimurium* Mutant Strain," *Journal of Microbiology, Immunology and Infection*, 2002, pp. 229-235, vol. 35, Issue 4.
Valentine, P. et al., "Identification of Three Highly Attenuated *Salmonella typhimurium* Mutants That Are More Immunogenic and Protective in Mice than a Prototypical aroA Mutant," *Infection and Immunity*, Jul. 1998, pp. 3378-3383, vol. 66, No. 7.

* cited by examiner

*Primary Examiner* — Oluwatosin Ogunbiyi
(74) *Attorney, Agent, or Firm* — Fenwick & West LLP

(57) ABSTRACT

The present invention relates to an attenuated *Salmonella typhi* having mutation in chromosomal gene loci, its use as a potent vaccine candidate to combat the *Salmonella* infection.

15 Claims, 8 Drawing Sheets

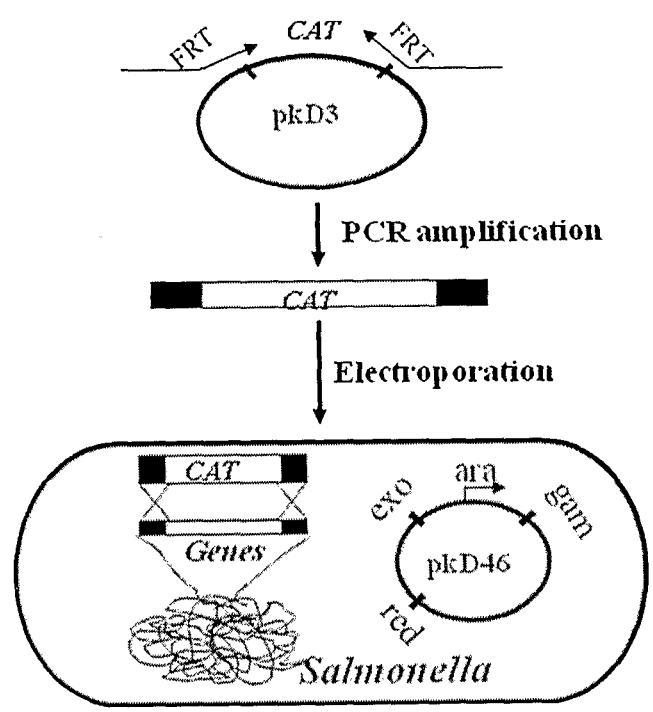
Fig: 1

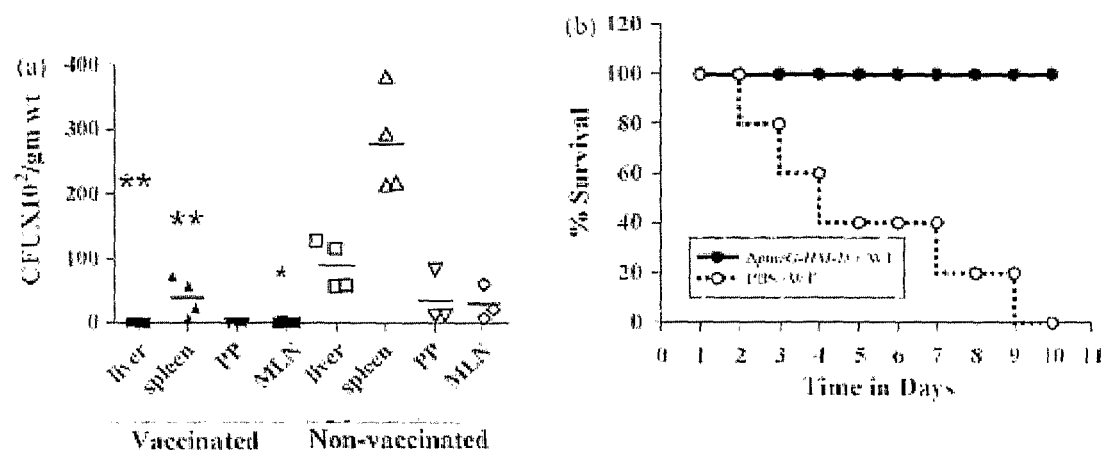
Fig: 2

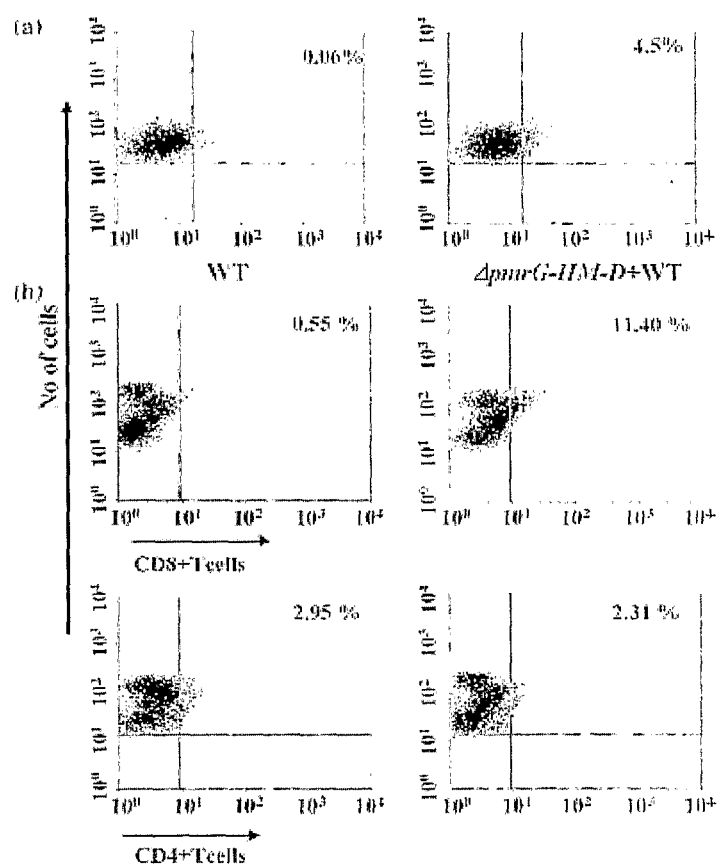
Fig: 3

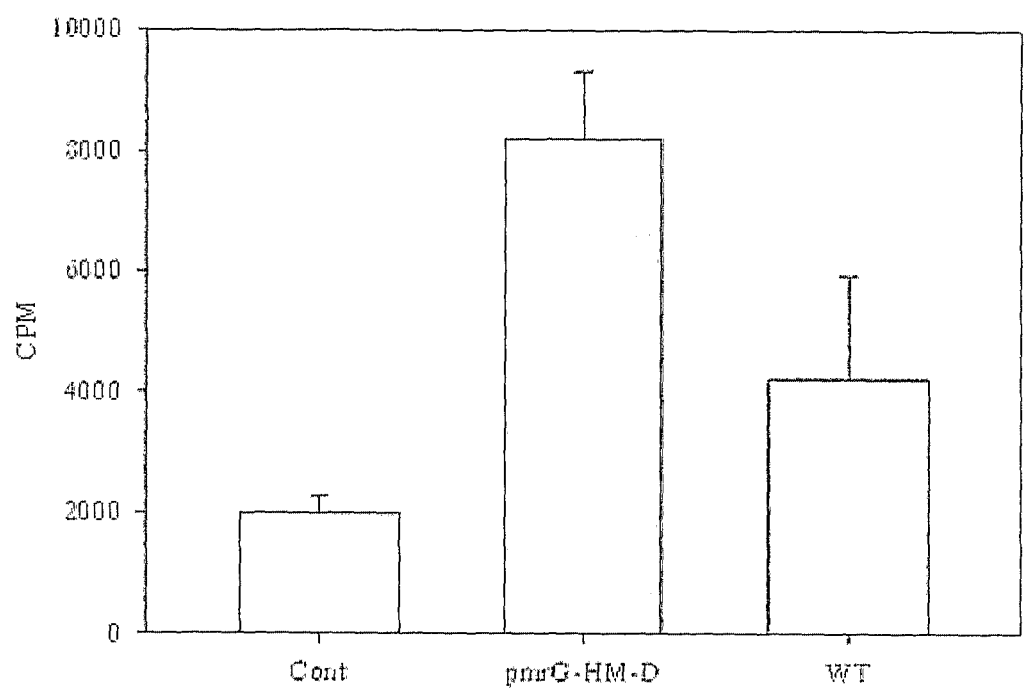
Fig: 4

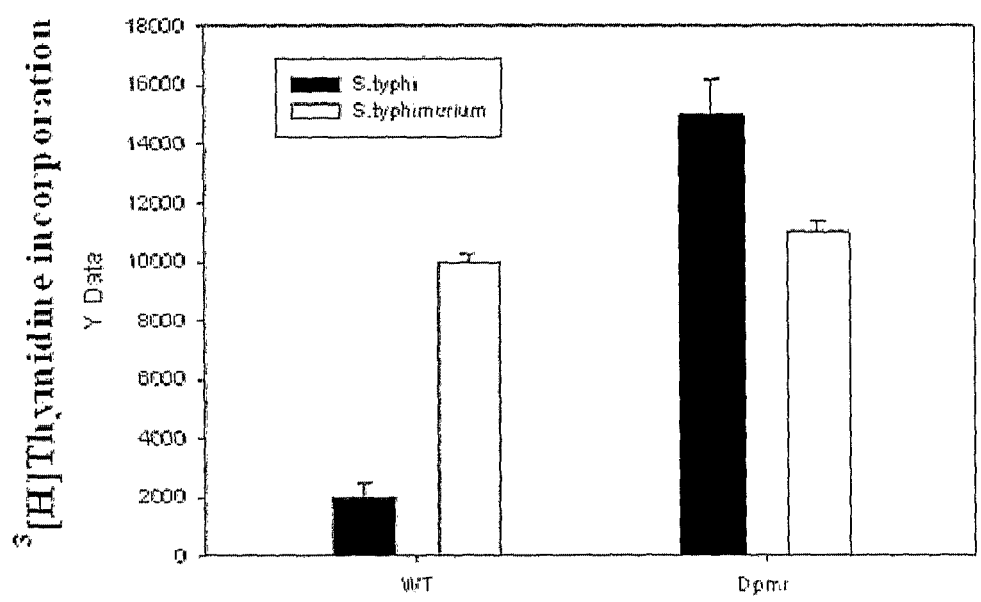
Fig: 5

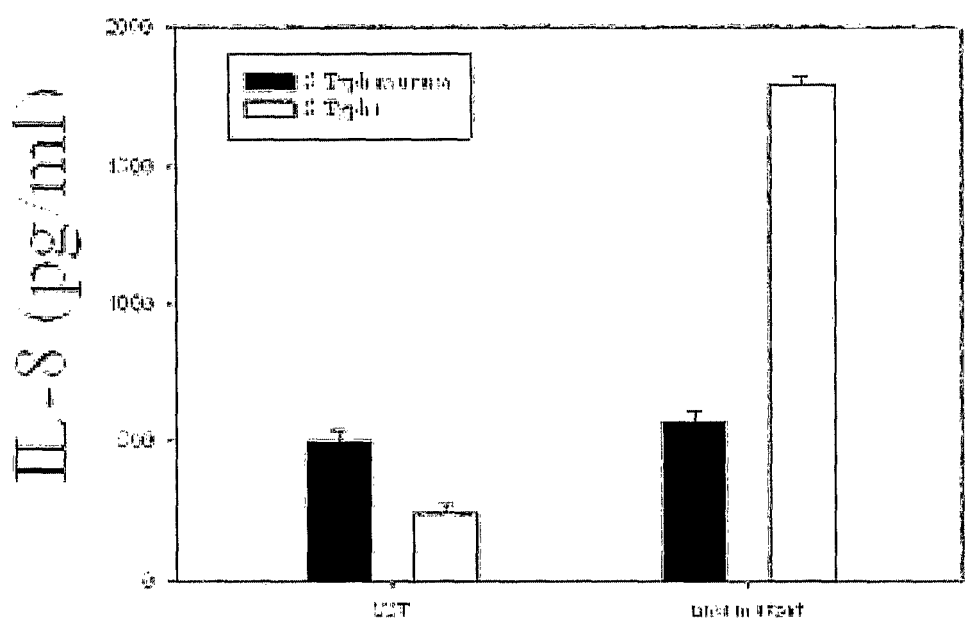
Fig: 6

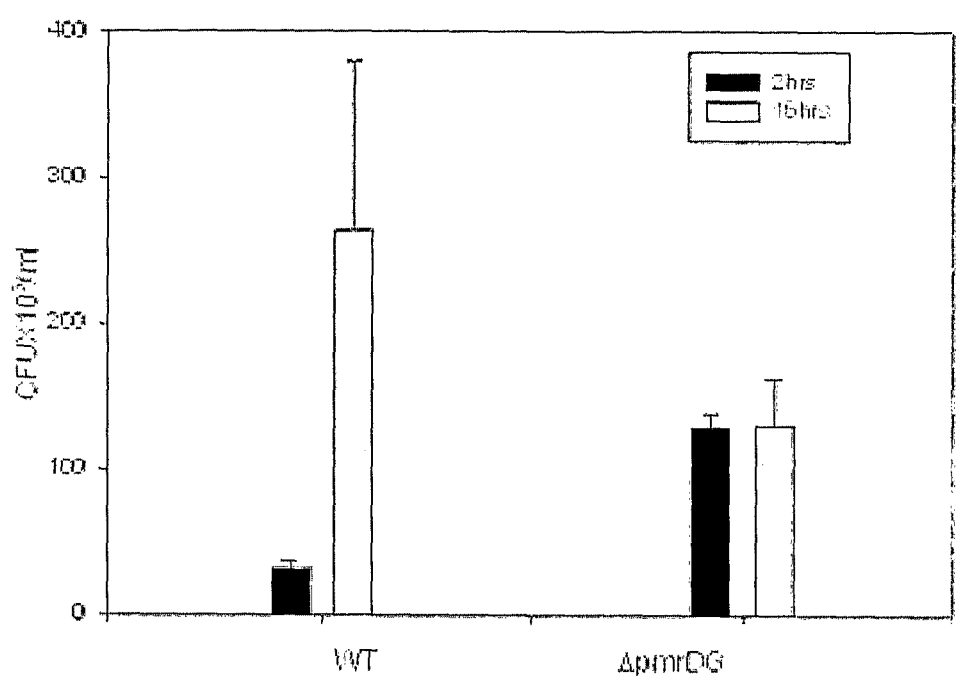
Fig: 7

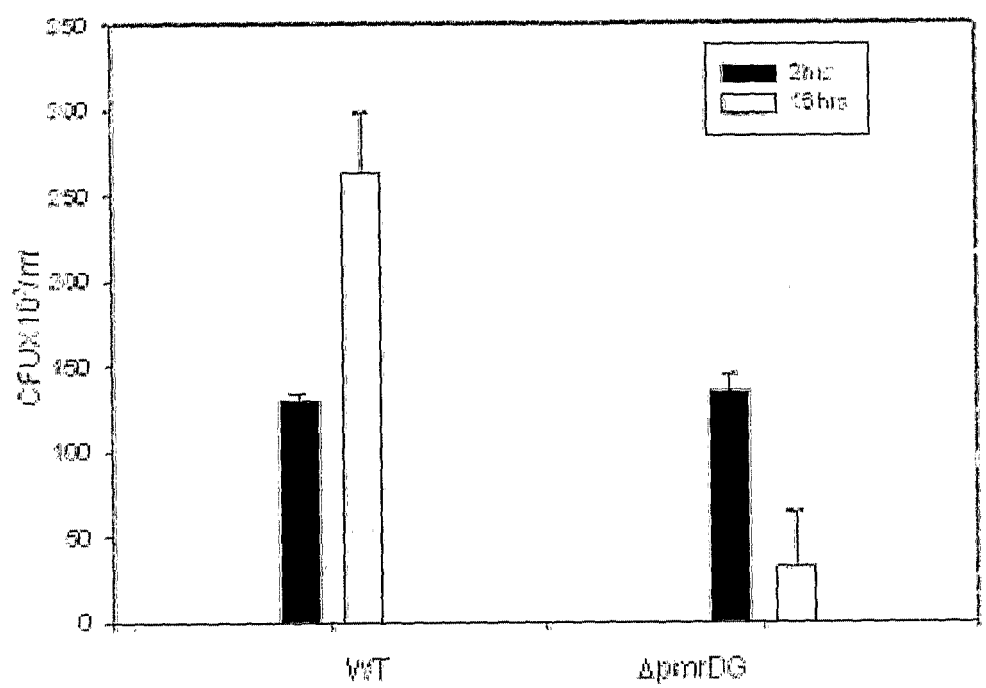
Fig: 8

MUTATED *SALMONELLA TYPHI* STRAIN AND USE THEREOF IN A VACCINE

FIELD OF THE PRESENT INVENTION

The present invention relates to an attenuated *Salmonella typhi* having mutation in chromosomal gene loci, its use as a potent vaccine candidate to combat the *Salmonella* infection.

BACKGROUND AND PRIOR ART OF THE INVENTION

*Salmonella typhi*, a causative agent of typhoid fever is raising a major threat due to its potential use in bioterrorism [Synder J W, American Society of Microbiology; 2000] and the non-availability of an efficient candidate vaccine. *Salmonella* species colonize several different host species. Some of the *Salmonella* species cause infections in specific hosts, whereas other *Salmonella* species have broad host range. *S. typhi* and *paratyphi* are strict pathogens of human. *S. dublin* cause disease in cattle, *S. abortus-equi* causes abortion in horses. *S. abortus-ovi* causes abortion in sheep. *S. choleraesuis* is major cause of lethal diarrhea in young pigs. *S. typhimurium* and *S. enteritidis* cause salmonellosis in human, poultry, pigs, cattle and rodents; *S. arizonae* causes disease in turkeys, whereas *S. gallinarum* causes salmonellosis only in poultry.

About 21.6 million people have suffered from typhoid and over 216,500 have succumbed to it, globally, in the year 2000 alone [Crump J A et. al. Bull World Health Organ 2004]. The incidence of typhoid is high (>100 cases per 100,000 population each year) in south-central Asia, southeast Asia and possibly southern Africa (10-100 cases per 100,000) [WHO 2004]. The increased appearance of antibiotic resistant strains of *Salmonella* further complicates the situation [Bhan M K et al., Lancet 2005].

The key to success for many bacteria in causing infection is colonization of host tissues. An enteric bacterium, such as *Salmonella*, gains entry through the oral route and survives the harsh environment of the intestine. At the intestinal mucosa, these bacteria encounter host defense mechanisms including antimicrobial peptides (AMPs), which are cationic, amphipathic molecules that kill bacteria by membrane permeabilization. Within the intestine, AMPs are secreted into the lumen by Paneth cells located in the base of intestinal crypts. AMPs are also found within phagocytic cells located in the intestinal submucosa. The ability of *Salmonella* to survive within the host intestine and within professional phagocytes is likely to depend, at least in part, on mechanisms of resistance to AMPs. The Pmr systems in *Salmonella* which includes pmrHIFJKLM, pmrD, pmrA-B, pmrE and pmrG are known to modify LPS, confer resistance to antimicrobial peptides and to regulate other two component regulatory system [Eguchi Y, et. al. Trends Biochem Sci 2005; 30: 70-2].

The *Salmonella* vaccine strains created so far had mutations in the metabolic genes or pathogenicity islands. *Salmonella* harboring mutations in SPI2 [Kirkpatrick B D, et. al. 2006 Vaccine 24:116-23], aro A [Khan S A, et. al. Vaccine 2006; 21:538-48.], hrtA [Tacket C O, Infect Immun 1997; 65:452-6] have been tested as a vaccine candidates in both animal models and humans. These vaccine candidates have not been able to fully protect the animals. The only licensed attenuated live oral typhoid vaccine, *S. typhi* strain Ty21a, is well tolerated and immunogenic, but requires three or four spaced doses of $2-6\times10^9$ CFU given every other day, an important practical shortcoming [Ivanoff B et. al. Bull WHO 1994; 72:957.26.]. Ty800, a vaccine strain, where phoP gene was knocked out, exhibited excellent protection in human volunteers [Miller S I, et. al. Vaccine 1993; 11(2): 122-5].

Previous literature shows mutated strains of *Salmonella enterica serovar Typhimurium* lacking pmrG-HM-D being studied (Negi V. D. et al, Vaccine. 2007 Jul. 20; 25(29):5315-23. Epub 2007 Jun. 4). However the model of experiment was a murine typhoid model against Salmonellosis caused by the organism.

Typhoid fever resulting from infection by *Salmonella typhi*, is a life threatening disease. An alarming increase in the antibiotic resistance and non-availability of a suitable vaccine further complicates the situation. Further, the threat to the pregnant women upon *Salmonella typhi* infection exists which involves loss of fetus or miscarriage.

Vi induces only short-lived antibody responses in children 2 to 5 years of age (unpublished data) and does not elicit protective levels in children younger than 2 years; in adults, reinjection after 2 years restores the level of vaccine-induced Vi antibody but does not elicit a booster response. These age-related and T-independent immunologic properties are similar to those of most polysaccharide vaccines.

Vi polysaccharide is coded by SPI7 island (*Salmonella* Pathogenecity Island 7). SPI7 is a mobile island and not all the strain of *S. typhi* harbors SPI7. Hence, it is not a good idea to develop vaccine against Vi, which is not found in all strains of *S. typhi*.

According to Prof Stefan Kaufmann, who is heading the Bill and Melinda Gates foundation, vaccine development project, reported that till now there is no efficient vaccine against *S typhi*.

With more than 16 millions of individuals getting infected with *S. typhi* each year, the threat continues to increase. *Salmonella typhi* has been classified as one of the organism for bioterrorism because of its life threatening extra-intestinal infection.

Keeping in mind the shortcomings, it is very important to generate a vaccine which can cover wide age groups, confer protective immunity and prevent abortion and still birth in pregnant females. The present invention thus covers and takes the appropriate measures to overcome the shortcomings reflected above.

OBJECTIVES OF THE INVENTION

The main objective of the present invention is to obtain *Salmonella typhi* having accession no. 5430 deposited at MTCC, Chandigarh.

Yet another objective of the present invention is to develop a process to obtain a mutant strain of *Salmonella typhi* having mutation in pmrG-HM-D chromosomal genomic loci.

Still another objective of the present invention is to obtain a vaccine comprising a mutant strain of *Salmonella typhi* having mutation in pmrG-HM-D chromosomal genomic loci.

Still another objective of the present invention is to obtain a method of vaccination.

Still another objective of the present invention is to obtain a kit for vaccination.

STATEMENT OF THE INVENTION

Accordingly, the present invention relates to a *Salmonella typhi* having accession no. 5430 deposited at MTCC, Chandigarh; a process to obtain a mutant strain of *Salmonella typhi* having mutation in pmrG-HM-D chromosomal genomic loci, said process comprises step of deleting the pmrG-HM-D chromosomal genomic loci from wild type *Salmonella typhi* to obtain the mutant strain; a vaccine comprising a mutant strain of *Salmonella typhi* having mutation in pmrG-HM-D chromosomal genomic loci: a method of vaccination, said method comprising step of administering therapeutically effective dose of vaccine comprising a mutant strain of *Salmonella typhi* to a subject in need thereof; and a kit for vaccination, said kit comprising the mutant strain of *Salmonella typhi*.

BRIEF DESCRIPTION OF ACCOMPANYING DRAWINGS

FIG. 1: Diagrammatic representation of production of mutant by lambda red recombination system.

FIG. 2: Dosage used in the study to check the CFU and viability of immunized and non-immunized mice.

FIG. 3: Enhanced antigen presenting capacity of vaccine as indicated by increase in CD8 T cell count.

FIG. 4: Antigen presentation in Caco-2 cells for WT and pmrK/O of *S. typhi*.

FIG. 5: Enhanced antigen presentation of WT and pmrDHMG mutant of *S. typhimurium* and *S. typhi* in human dendritic cells.

FIG. 6: IL-8 production in Caco-2 cells upon infection with WT and mutant strains of *S. typhimurium* and *S. typhi*.

FIG. 7: Intracellular survival assay for *S. typhimurium* WT and pmrDG in mouse RAW macrophages FIG. 8: Intracellular survival assay for *S. typhi* WT and pmrDG in THP-1 human macrophages

DETAILED DESCRIPTION OF THE INVENTION

The present invention relates to a *Salmonella typhi* having accession no. 5430 deposited at MTCC, Chandigarh.

In another embodiment of the present invention, the *Salmonella typhi* is a mutant strain obtained by deletion of pmrG-HM-D chromosomal genomic loci, corresponding to ST2527-ST2534 region of the chromosomal genome.

The present invention relates to a process to obtain a mutant strain of *Salmonella typhi* having mutation of pmrG-HM-D chromosomal genomic loci, said process comprises step of deleting the pmrG-HM-D chromosomal genomic loci from wild type *Salmonella typhi* to obtain the mutant strain.

In another embodiment of the present invention, the mutation of pmrG-HM-D chromosomal genomic loci comprises steps of:
a. amplifying chloramphenicol acetyl transferase cassette of plasmid with primers having overhangs of flanking regions of pmrG-HM-D; and
b. transforming *Salmonella typhi* having red helper plasmid with the amplified chloramphenicol acetyl transferase cassette.

In yet another embodiment of the present invention, the plasmid used for amplifying chloramphenicol acetyl transferase cassette is pKD3.

In still another embodiment of the present invention, the red helper plasmid is pKD46.

In still another embodiment of the present invention, the mutant strain of *Salmonella typhi* is obtained by deletion of pmrG-HM-D chromosomal genomic loci, corresponding to ST2527-ST2534 region of the chromosomal genome.

The present invention relates to a vaccine comprising a mutant strain of *Salmonella typhi* having mutation in pmrG-HM-D chromosomal genomic.

In yet another embodiment of the present invention, the mutant strain of *Salmonella typhi* is obtained by deletion of pmrG-HM-D chromosomal genomic loci, corresponding to ST2527-ST2534 region of the chromosomal genome.

In still another embodiment of the present invention, the vaccine is in a capsular form.

The present invention relates to a process to obtain a method of vaccination, said method comprising step of administering therapeutically effective dose of vaccine comprising a mutant strain of *Salmonella typhi* to a subject in need thereof.

In yet another embodiment of the present invention, the mutant strain of *Salmonella typhi* is obtained by deletion of pmrG-HM-D chromosomal genomic loci, corresponding to ST2527-ST2534 region of the chromosomal genome.

In still another embodiment of the present invention, the vaccine is administered through oral route or intra peritoneal route.

In still another embodiment of the present invention, the vaccine is administered in capsular form.

In still another embodiment of the present invention, the vaccine is administered at a dosage ranging from about $10^3$ and $10^{10}$ CFU, preferably ranging from about $10^6$ and $10^9$ CFU.

In still another embodiment of the present invention, the vaccine is live attenuated vaccine and essentially provides about 100% protection against *Salmonella* infections.

In still another embodiment of the present invention, the vaccine is capable of combating localized and systemic *Salmonella* infection(s) in animals, including humans.

In still another embodiment of the present invention, the vaccine provides protection against abortion in animals, including humans.

The present invention relates to a kit for vaccination, said kit comprising the mutant strain of *Salmonella typhi*.

The present invention relates to the live attenuated vaccine of *Salmonella typhi*, which is highly attenuated in vivo. The vaccine strain is able to provide very good immune response against the challenge of virulent *Salmonella*. Also the vaccine strain studies done make this strain as a potent vaccine candidate.

The vaccine strain generated in the present invention, provides a very good protection and is safe and efficacious. The vaccine strain DV-ST-07 is capable of giving a very good protection and can trigger the immune system, enabling the organism to encounter the wild-type challenge. The vaccine strain invented in present study is unable to modify LPS and is more sensitive to antimicrobial peptides as compared to its wild-type counterpart but is able to provide protection against *Salmonella* challenge when given through oral and intra peritoneal route. The useful dosage to be administered will vary depending on the age, weight and animal vaccinated, the mode and route of administration and the type of pathogen against which vaccination is sought. The vaccine may comprise any dose of bacteria, sufficient to evoke an immune response. Doses ranging between $10^3$ and $10^{10}$ bacteria are e.g. very suitable doses. Doses between $10^6$ and $10^9$ bacteria are even more preferred. The dose used in our study ranges from $10^3$-$10^4$ bacteria.

The present invention claims a very potent vaccine candidate against *Salmonella typhi* which harbors multiple mutations. The intricate network among paw systems have helped us create a multiple mutant of *Salmonella typhi* (ΔpmrGHM-D) which is highly attenuated and does not cause disease even at higher doses on oral and intraperitoneal administration. These mutations are in the virulence gene in *Salmonella typhi*. Mutating these genes will render *S. typhi* non-infectious. The mutations in these particular genes will further enhance the antigen-presenting capacity of *S. typhi*, which will in turn provide long-term protection to the host. This vaccine will require low-dose and can be suitable for administration in pregnant women. The cost is very minimal and the manpower required is very less.

The present invention therefore provides for a potent vaccine candidate which can induce long term protection, prevent miscarriage and is needed to be administered in low dose.

The vaccine strain of the present invention is able to provide a very good protection against wild-type challenge followed by single and multiple doses of vaccination of mice model. The requirement of dose is also very low as compared to other existing vaccine, thus the invented vaccine strain can act as a very potent and efficacious vaccine candidate.

The vaccine strain generated is capable of providing very good protection and does not require any adjuvant to enhance the immune response.

Thus the more preferred form of vaccine is live attenuated vaccine without any adjuvant in a capsular form.

According to our invention the route of administration of vaccine to human is oral or intraperitoneal.

The gene locus pmrG-HM-D is present in other strains of *Salmonella* also. Gene sequence of *Salmonella typhi* was blasted with the known complete sequence of *Salmonella* species like *Salmonella typhi* CT18, *Salmonella typhi* Ty2, *Salmonella paratyphi*. About 98-99% similarities were observed in the sequence, thus the gene can be immobilized in other strains also.

The strain is deposited with MTCC, an International Depository located at Chandigarh, India.

| Identification Reference Assigned | MTCC Number |
|---|---|
| *Salmonella enterica* serovar *Typhi* DV-ST-07 | MTCC 5430 |

Date of Deposit: Jul. 1, 2008

Name and Complete Address of the Depository Authority:

Microbial Type Culture Collection & Gene Bank
Institute of Microbial Technology
Sector 39-A, Chandigarh-160 036
India The invention is further elaborated with the help of following examples. However, these examples should not be construed to limit the scope of the invention.

EXAMPLES

Example 1

The mutants of *Salmonella typhi* were generated by using lambda red recombination system. CAT cassette was amplified by PCR amplification from pKD3 plasmid in *E. coli*, amplified product was transformed in to *Salmonella* competent cells. Genes are replaced by the cassette with homologous recombination. (FIG. 1). Mutant were screened by plating on Chloramphenicol (Chl) plate and confirmed by doing colony PCR and used for experiment under selection condition of Chl (20 μg/ml). The mutant strain of *Salmonella typhi* was generated by replacing the gene from ST2527-ST2534.

*Salmonella* transformants carrying a red helper Plasmid (pKD46) were grown in LB with carbencillin and 10 mM L-arabinose at 30° C. When the cells reach an OD (600 nm) of 0.4-0.5, electrocompetent cells were made by washing three times with ice-cold autoclaved milli Q water and 10% glycerol. The chloramphenicol cassette (CAT) of pKD3 was amplified with primers having overhangs of flanking regions of pmrGMHD. This PCR product was electroporated into *Salmonella typhi* having pKD46. Immediately after electroporation, 1 ml of SOC was added and incubated at 37° C. for 1 h before plating on to the LB-agar plates containing chloramphenicol (50 μg/ml). Mutants were selected by virtue of their ability to grow on the antibiotic plates and confirmed by colony PCR using specific confirmatory primers and cassette internal primer.

Example 2

Dosage used in the present study is $10^3$ cfu for intra-peritoneal and $10^4$ cfu of the vaccine strain for oral immunization followed by lethal and sub lethal dose of $10^8$ and $10^7$ cfu of challenge wild type organism respectively to check the CFU and viability of immunized and non-immunized mice (FIG. 2).

CD4+ and CD8+ cell count was also analyzed and significant increase in CD8+ cell in spleen of immunized mice as compared to non-immunized mice was observed.

$CD4^+$ and $CD8^+$ cell counts were checked in vaccinated mice and a significant increase in $CD8^+$ cell count, which can contribute to the long-term protective immunity against *Salmonella typhi*, in vaccinated mice when compared with non-vaccinated mice was observed. The CD8 T cell counts of the vaccinated mice are very high showing that the antigen presentation is robust and only one dose of this vaccine strain is able to protect the mice from typhoid fever (FIG. 3). The enhanced lymphocyte response is correlated with increased antigen presentation in the case of our vaccine strain leading to good immune response. When antigen presentation of vaccine strain was checked in human epithelial cell line Caco-2 in a mixed lymphocyte reaction, increased antigen presentation in case of vaccine strain was observed. This explains the increased immune response in vaccinated mice.

One more important observation was the induction of abortion in pregnant mice by the WT *Salmonella typhi* and not by vaccine strain. These finding strongly suggests that the vaccine strain appears to be safe even in pregnant individuals.

Thus, the vaccine strains DV-ST-07 of present invention is very potent vaccine candidate against *Salmonella* infection.

Example 3

Antigen presentation in Caco-2 cells for WT and pmrK/O of *S. Typhi*: Caco-2 cells are excellent model system which mimics the human small intestinal epithelial cells in vivo. Caco-2 cells were used as antigen presenting cells. Caco-2 cells were infected with 1:10 MOI of either WT or pmr knockout strain of *Salmonella Typhi*. After 30 mins of infection the extracellular bacteria were killed by gentamicin and further incubated for 24 hrs. PBMC from health human donors were added to the infected cells and pulsed with tritiated thymidine for 72 hrs. PBMCs were harvested and the thymidine incorporation was measured by using liquid scintillation counter. As shown in FIG. 4, the pmr knock out strain has better capacity to present antigen than the WT strain.

Example 4

There were no side effects of the vaccination in the mice model used for study. From the table 1 below, it is very evident that the vaccine is safe for use in the pregnant women and it protects the fetus from getting aborted.

TABLE 1

| Strain used | No of mice | Death | Mice Aborted | Pup delivered | Pup died 0-10 | Death after delivery 10-20 days | CFU of Pups (Uninfected) | CFU of Pups (Iinfected) |
|---|---|---|---|---|---|---|---|---|
| WT | 6 | 1 | 3 | 3 | 0 | | | |
| Salmonella | | | | 12 | 3 | (9 dead) | | |
| | | | | — | — | | Very High | Low |
| | | | | — | — | | | |
| ΔpmrG-HM-D | 6 | 0 | 2 | 12 | 3 | no death | | |
| | | | | — | 0 | — | | |
| | | | | — | 0 | — | — | |
| | | | | — | 0 | — | | Low |
| PBS | 5 | 0 | 0 | 12 | 3 | — | | |
| | | | | 15 | 4 | — | | |
| | | | | — | — | | | |
| | | | | — | — | | | Very high |
| | | | | — | — | | | |

Example 5

The Mutations of the pmr sysytem were studied in *Salmonella typhimurium* and results were compared with those of *Salmonella typhi*. It is observed that the behavior of *S. typhimurium* and *S. typhi* strains carrying mutation in pmrDHMG is completely different in the human dendritic cells and human intestinal epithelial cell line Caco-2 cells. On one hand the *S. typhi* WT strain inhibits antigen presentation in the human dendritic cells, whereas the mutant strain of *S. typhi* enhances the antigen presentation. However *S. typhimurium* WT strain and mutant strain do not show any difference in their activities and the mutant strain does not enhance the antigen presentation in the human dendritic cells. (FIG. 5)

Example 6

IL-8 is a chemokine which attracts neutrophil in an immune response. Comparative studies of two genera of *Salmonella* were carried out. It is observed that *S. typhimurium* WT and mutant strain have no difference in the IL-8 level when compared to *S. typhi*. *S. typhi* WT strain induces no IL-8 response whereas the mutant strain induces high level of IL-8. IL-8 was measured in the supernatant of infected cells by using the IL-8 ELISA kit from BD (Becton and Dickinson). (FIG. 6)

Example 7

The growth pattern of the mutation in pmrDG leads of *S. typhi* and *S. typhimurium* leads to two different phenotype in mouse and human specific macrophages. As shown in FIG. 7, the mutation of pmrD-HM-G in *S. typhimurium* leads to no difference in growth in the mouse macrophages cell line RAW 264.7 cells. Mice model is the model system for studying *S. typhimurium*. However FIG. 8 demonstrates completely different effect in terms of growth of the pmr-D-HM-G mutant in *S. typhi* using human specific macrophages THP-1.

The data indicated above (examples 5, 6 and 7) points out to very important phenomena that it is not expected under ordinary circumstances that the genes in *Salmonella* species, for two different genera, would work in a similar way.

REFERENCES

1. Synder J W, Check W. Bioterrorism threats to our future. A report from American Society of Microbiology, 2000.
2. Crump J A, Luby S P, Mintz E D. The global burden of typhoid fever. *Bull World Health Organ* 2004; 82:346-53.
3. Bhan M K, Bahl R, Bhatnagar S. Typhoid and paratyphoid fever. Lancet. 2005; 366:749-62.
4. Kirkpatrick B D, McKenzie R, O'Neill J P, et al. Evaluation of *Salmollella enterica* serovar Typhi (Ty2 aroC-ssaV-) M01ZH09, with a defined mutation in the *Salmonella* pathogenicity island 2, as a live, oral typhoid vaccine in human volunteers. Vaccine. 2006; 24: 116-23.
5. Khan S A, Stratford R, Wu T, et al. *Salmonella typhi* and *S. typhimurium* derivatives harbouring deletions in aromatic biosynthesis and *Salmonella*. Pathogenicity Island-2 (SP1-2) genes as vaccines and vectors. Vaccine. 2003; 21:538-48.
6. Tacket C O, Sztein M B, Losonsky G A, Wasserman S S, Nataro J P, Edelman R, Pickard D, Dougan D, Chatfield S N, and Levine M M. Safety of live oral *Salmollella typhi* vaccine strains with deletions in htrA and aroC aroD and immune response in humans. Infect. Immun 1997; 65:452-6.
7. Ivanoff, B., M. M. Levine, and P. H. Lambert. 1994. Vaccination against typhoid fever: present status. *Bull W. H.* 0.72:957.26.
8. Miller S I, Loomis W P, Alpuche-Aranda C, Behlau I, Hohmann E. The PhoP virulence regulon and live oral *Salmonella* vaccines. Vaccine 1993; 11(2):122-5.
9. Nagy G, Dobrindt U, Hacker J, Emody L. Oral immunization With an rfaH mutant elicits protection against salmonellosis in mice. Infect Immun 2004; 72:4297-301.
10. jTang I K, Ji D D, Chou C F, Lin H C, Liao C L, Sytwu H K, et al. Characterization of a highly attenuated *Salmonella enterica* serovar *Typhimurium* mutant strain. J Microbiol Immunol Infect 2002; 35:229-35.
11. Valentine P J, Devore B P, Heffron F. Identification of three highly attenuated *Salmonella typhimurium* mutants that are more immunogenic and protective in mice than a prototypical aroA mutant. Infect Immun 1998; 66:3378-83.
12. Datsenko K A, Wanner B L. One-step inactivation of Chromosomal genes in *Escherichia coli* K-12 using PCR products. Proc Natl Acad Sci USA 2000; 97(June (12)): 6640-5.

We claim:

1. A *Salmonella typhi* having accession no. 5430 deposited at MTCC, Chandigarh.

2. A process to obtain a *Salmonella typhi* strain of claim 1, said process comprises step of deleting the pmrG-HM-D chromosomal genomic loci from wild type *Salmonella typhi* to obtain the mutant strain.

3. The process of claim 2, wherein the deletion of pmrG-HM-D chromosomal genomic loci comprises steps of:

a. amplifying chloramphenicol acetyl transferase cassette of a plasmid with primers having overhangs of flanking regions of pmrG-HM-D, and b. transforming *Salmonella typhi* having red helper plasmid with the amplified chloramphenicol acetyl transferase cassette.

4. The process of claim 3, wherein the plasmid used for amplifying chloramphenicol acetyl transferase cassette is pKD3.

5. The process of claim 3, wherein the red helper plasmid is pKD46.

6. A vaccine comprising a mutant strain of *Salmonella typhi* with accession no. 5430 deposited at MTCC, Chandigarh, having a deletion in pmrG-HM-D chromosomal genomic loci.

7. The vaccine of claim 6, wherein the vaccine is in a capsular form.

8. A method of vaccination, said method comprising a step of administering a therapeutically effective dose of vaccine comprising a *Salmonella typhi* strain of claim 1 to a subject in need thereof.

9. The method of claim 8, wherein the vaccine is administered through oral route or intra peritoneal route.

10. The method of claim 8, wherein the vaccine is administered in capsular form.

11. The method of claim 8, wherein the vaccine is administered at a dosage ranging from $10^3$ to $10^{10}$ CFU.

12. The method of claim 8, wherein the vaccine is live attenuated vaccine and provides for 100% survival against *Salmonella typhi* infection in a vaccinated subject.

13. The method of claim 8, wherein the vaccine is capable of preventing localized and systemic *Salmonella typhi* infection in animals.

14. The method of claim 8, wherein administering the vaccine reduces the number of abortions caused by *Salmonella typhi* in animals compared with the number of abortions caused by *Salmonella typhi* in animals that are administered a vaccine having the wild-type strain of *Salmonella typhi*.

15. The method of claim 11, wherein the vaccine is administered at a dosage ranging from $10^6$ to $10^9$ CFU.

* * * * *